US005633406A

United States Patent [19]
Mitchell et al.

[11] Patent Number: 5,633,406
[45] Date of Patent: May 27, 1997

[54] VICARIOUS NUCLEOPHILIC SUBSTITUTION USING 4-AMINO-1,2,4-TRIAZOLE, HYDROXYLAMINE OR O-ALKYLHYDROXYLAMINE TO PREPARE 1,3-DIAMINO-2,4,6-TRINITROBENZENE OR 1,3,5-TRIAMINO-2,4,6-TRINITROBENZENE

[75] Inventors: Alexander R. Mitchell; Philip F. Pagoria; Robert D. Schmidt, all of Livermore, Calif.

[73] Assignee: The Regents of the University of California, Oakland, Calif.

[21] Appl. No.: 440,024

[22] Filed: May 12, 1995

[51] Int. Cl.[6] .................................................. C07C 209/02
[52] U.S. Cl. ....................... 564/395; 568/932; 568/934; 564/408
[58] Field of Search ..................... 564/395; 568/932, 568/933, 934

[56] References Cited

U.S. PATENT DOCUMENTS

| | | | |
|---|---|---|---|
| H1078 | 7/1992 | Norris et al. | 548/126 |
| H1304 | 4/1994 | Norris et al. | 548/126 |
| 3,278,604 | 10/1966 | Hoffman. | |
| 3,394,183 | 7/1968 | Dacons. | |
| 4,032,377 | 6/1977 | Benziger. | |
| 4,248,798 | 2/1981 | Atkins. | |
| 4,952,733 | 8/1990 | Ott. | |
| 5,262,539 | 11/1993 | Makosza et al. | 546/307 |
| 5,466,871 | 11/1995 | Seko | 564/395 |

FOREIGN PATENT DOCUMENTS 3612238  10/1987  Germany.

OTHER PUBLICATIONS

O. Westphal, "Uber die Alkylierung des Hydrazins," *Ber.* vol. 74 (1941), p. 759.

E. Y. Spencer, et al., "Preparation of Pyramide," *Can. J. Res.*, vol. 24B (1946) pp. 204–207.

J.R. Holden, et al., "Heat Resistant Explovies VI: Properties of 1,3–Diamino–2,4,6–Trinitrobenzene, DATB," *NAVORD Report 6299* (Mar. 17, 1959).

G.M. Omietanski, et al., "The Reaction of Chloramine with Tertiary Amines. 1,1,1–Trisubstituted Hydrazinium Salts," *J.ACS.*, vol. 78 (1956) pp. 1211–1213.

S.K. Yasuda, "Identification of 1,3,5–Triamino–2,4,6–Trinitrobenzene Impurities by Two–Dimensional Thin–Layer Chromatography," *Journal of Chromatography*, vol. 71 (1972), pp. 481–486.

T. Urbanski and S.K. Vasudeva, "Heat Resistant Explosives," *Journal of Scientific Industrial Research*, vol. 37 (May 1978), pp. 221–280.

W.P. Norris and A.P. Chatin, "CL–14, A New Dense, Insensitive, High Explosive (u)," *NWC TP 6597* (May 1985).

R.L. Atkins, et al., "Synthesis of Polynitro Compounds. Hexasubstituted Benzenes," *J. Org. Chem.* vol. 51 (1986), pp. 3261–3266.

M. Makosza, et al., "Vicarious Nucleophilic Substitution of Hydrogen," *Acc. Chem. Res.* vol. 20 (1987), pp. 282–289.

W. Worthy, "Shock Sensitivity of Explosives Clarified," *C&EN*, Aug. 10, 1987, p. 25.

M. Makosza, "Amination of Nitroarenes with Sulfenamides via Vicarious Nucleophilic Substitution of Hydrogen," *J. Org. Chem.*, vol. 57 (1992) pp. 4784–4885.

A.R. Mitchell, et al., "Advances in the Chemical Conversion of Energetic Materials to Higher Value Products," *Presentation at Life Cycles of Energetic Materials*, Del Mar, CA, Dec. 11–16, 1994.

J.G. Keay, et al., "Regiospecific synthesis of 1–substituted–1,2,4–triazoles using 4–amino–1,2,4–triazole".

Katritzky et al., J. Org. Chem. 1986, vol. 51, 5039–5040.

Katrizky et al., J. Org. Chem. 1988, vol. 53, 3978–3982.

Mitchell et al., 24th Intl. Annual. Conference of ICT, Karlsruhe, Germany, pp. 38–1–38–6.

Price et al., Organic Syntheses, Coll. vol. III, pp. 664–665.

*Primary Examiner*—Charles T. Jordan
*Assistant Examiner*—John R. Hardee
*Attorney, Agent, or Firm*—Henry P. Sartorio

[57] ABSTRACT

The present invention relates to a process to produce 1,3-diamino-2,4,6-trinitrobenzene (DATB) or 1,3,5-triamino-2,4,6,-trinitrobenzene (TATB) by:

(a) reacting at ambient pressure and a temperature of between about 0° and 50° C. for between about 0.1 and 24 hr, a trinitroaromatic compound of structure V:

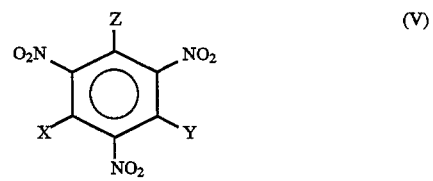

(V)

wherein

X, Y, and Z are each independently selected from the group consisting of —H and —$NH_2$, with the proviso that at least 1 or 2 of X, Y, and Z are hydrogen;

with an effective amount of 1-amino-1,2,4-triazole, hydroxylamine or O-alkylhydroxamine to produce DATB or TATB;

in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of methanol, ethanol, propanol, butanol, dimethylsulphoxide, N-methylpyrrolidone, hexamethylphosphoramide, dimethylformide, dimethylacetamide and mixtures thereof, provided that when alcohols are present or when hydroxylamine or its O-alkyl derivatives replace ATA primarily DATB is formed; and (b) isolating the DATB or TATB produced. DATB and TATB are important and useful specialty explosives and intermediates for other materials.

20 Claims, No Drawings

VICARIOUS NUCLEOPHILIC SUBSTITUTION USING 4-AMINO-1,2,4-TRIAZOLE, HYDROXYLAMINE OR O-ALKYLHYDROXYLAMINE TO PREPARE 1,3-DIAMINO-2,4,6-TRINITROBENZENE OR 1,3,5-TRIAMINO-2,4,6-TRINITROBENZENE

ORIGIN OF THE INVENTION

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

1. Field of the Invention

The present invention concerns the use of 4-amino-1,2,4-triazole, as well as hydroxylamine and its O-alkyl derivatives, to provide new and improved syntheses of DATB and TATB by vicarious nucleophilic substitution (VNS) reactions.

2. Description of the Problem and Related Art

Some explosives are more sensitive to shock and heat than others having a similar structure. Studies of explosives based on the benzene ring include, for example, 1,3,5-trinitrobenzene (TNB), 2,4,6-trinitrotoluene (TNT), 1-monoamino-2,4,6-trinitrobenzene (MATB) (aka picramide), 1-3-diamino-2,4,6-trinitrobenzene (DATB) and 1,3,5-triamino-2,4,6-trinitrobenzene (TATB). Although these compounds have much in common, the shock initiation thresholds, that is, the shock pressure required to cause detonation in 50% of the tests, vary widely. Table 1 shows the pattern.

TABLE 1

| SHOCK INITIATION THRESHOLD OF EXPLOSIVES | |
|---|---|
| Compound | Pressure (kilobars) |
| TNB | 17 |
| TNT | 21 |
| MATB | 30 |
| DATB | 46 |
| TATB | 75 |

While not wanting to be bound by theory, it appears that adding amino groups to a nitro-substituted benzene ring raises the initiation shock threshold. This pattern occurs, because as the networks of hydrogen bonds increase, the networks absorb energy from a shock front and reduce the amount of shock that goes to the ring itself. See W. Worthy in "Shock Sensitivity of Explosives Clarified", *Chemical and Engineering News*, p. 25, (Aug. 10, 1987) for further discussion.

It follows that DATB and TATB are highly desirable, insensitive explosives that are used primarily in specialty applications. Part of the reason that they are used in special as opposed to general explosive applications is high cost.

They are too expensive to use in ordinary applications when other less expensive explosives can be used. One reason that TATB is expensive is that it is usually prepared from 1,3,5-trichlorobenzene which is expensive and is not generally available from domestic suppliers. The chloride byproduct ($NH_4Cl$) is difficult to remove and may cause compatibility problems in certain types of ordnance (cf. U.S. Pat. No. 4,032,377).

TATB is also valuable in non-explosive applications. K. Praefake and B. Kohne, Ger. Often. DE 3,612,238 disclose the use of TATB to prepare hexaaminobenzene derivatives which are used as components of lyotropic liquid-crystal phases, which can be used in display devices.

Alternative preparations were also sought, and

T. M. Benziger, U.S. Pat. No. 4,032,377 discloses a preparation of TATB by nitration of 1,3,5-trichlorobenzene to 1,3,5-trichloro-2,4,6-trinitrobenzene followed by treatment with ammonia to produce TATB. This patent also discloses the use of water to separate the byproduct ammonium chloride.

D. G. Ott and T. M. Benziger, U.S. Pat. No. 4,952,733 and *Journal of Energetic Materials*, vol. 5, pp. 343–354 (1987) disclose a preparation of TATB by nitration of 3,5-dichloroanisole to produce 3,5-dichloro-2,4,6-trinitroanisole which is chlorinated to give 1,3,5-trichloro-2,4,6-trinitrobenzene which is ammonolyzed to give TATB.

Additional art of interest includes, for example:

R. T. Atkins et al., in U.S. Pat. No. 4,248,798 disclose a new method for preparing pentanitroaniline (PNA) and triaminotrinitrobenzene (TATB) from TNT. TNT is first reduced using $H_2S$ to 4-amino-2,6-dinitrotoluene then nitrated using nitric acid/sulfuric acid to pentanitroaniline followed by reaction with ammonia to produce the TATB.

J. Meisenheimer et al., in *Chemische Berichte*, vol. 39, pp. 2533–2542 (1906) describe the di-amination of 1,3-dinitrobenzene with hydroxylamine under basic conditions to yield 2,4-dinitro-1,3-phenylenediamine.

M. Makosza et al., review and discuss "Vicarious Nucleophilic Substitution of Hydrogen", in *Accounts of Chemical Research*, vol. 20, pp. 282–9 (1987), and teach the substitution of polynitrobenzene structures with a number of non-nitrogen containing vicarious nucleophilic substitution reagents. No nitrogen-containing reagents are suggested.

A. R. Katritzky and K. S. Laurenzo, *Journal of Organic Chemistry*, vol. 51, pp. 5039–5040 (1986) disclose monoamination of nitrobenzene and some substituted nitrobenzenes to give 4-nitroanilines by VNS reactions using 4-amino-1,2,4-triazole. The same authors, in the *Journal of Organic Chemistry*, vol. 53, pp. 3978–3982 (1988) disclose the use of a series of 4-(alkylamino)-1,2,4-triazoles to transfer the alkylamino group to the 4-position of nitrobenzene and 3-substituted nitrobenzenes by VNS.

J. A. Hoffman and C. F. McDonough, U.S. Pat. No. 3,278,604 and J. C. Dacons et al., in U.S. Pat. No. 3,394,183 both disclose the preparation of DATB via sulfonation and nitration (2 steps) of 1,3-dimethoxy-2,4,6-trinitrobenzene (DMTNB) which is then aminated to give DATB.

T. Urbanski et al., *Journal of Scientific and Industrial Research* (India), vol. 37, p. 250–5 (1978), disclose the standard preparation and properties of several heat resistant explosives including DATB and TATB.

J. R. Holden et al., U.S. Naval Ordnance Laboratory, White Oak, Md., NAVORD Report 6299 (March 1959), disclose the properties of DATB.

S. K. Yasuda et al., in *Journal of Chromatography*, vol. 71, p. 484–86 (1972) discuss the separation and identification of 12 impurities of 1,3,5-triamino-2,4,6-trinitrotoluene by two dimensional thin-layer chromatography.

M. Makosza et al., *Journal of Organic Chemistry*, vol. 57, p. 4784–5 (1992), disclose the mono-amination of nitrobenzenes with sulfenamides via vicarious nucleophilic substitution of hydrogen.

W. P. Norris et al., "CL-14, A New Dense, Insensitive, High Explosive", Naval Weapons Center, China Lake, Calif., Report No. TP 6597 (Unclassified), May 1985, disclose the use of hydroxylamine under basic conditions to di-aminate 4,6-dinitrobenzofuroxan (DNBF) thereby producing 5,7-diamino-4,6-dinitrobenzofuroxan (CL-14).

R. T. Atkins et al., in the *Journal of Organic Chemistry*, vol. 51, pp. 3261–3266 (1986), disclose the synthesis of a number of polynitro compounds, including TATB. Pentanitroaniline is reacted with ammonia to produce TATB.

J. G. Kaey and E. F. V. Scriven in Chemical Specialties USA 91 Symposium disclose the regiospecific synthesis of 1-substituted-1,2,4-triazoles using 4-amino-1,2,4-triazole.

None of these references individually or collectively teach or suggest the present invention.

It is apparent from this description that there is a need for new processes to easily convert nitroaromatic compounds to DATB, TATB or mixtures thereof. The present invention provides such useful processes which are also environmentally benign.

SUMMARY OF THE INVENTION

The present invention relates to a process to produce 1,3-diamino-2,4,6-trinitrobenzene (DATB) or 1,3,5-triamino-2,4,6,-trinitrobenzene (TATB) by:

(a) reacting a temperature of between about 0° and 50° C. for between about 0.1 and 24 hr, a trinitroaromatic starting material compound of structure V:

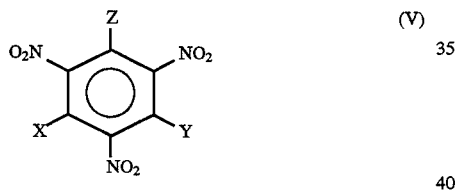

wherein

X, Y, and Z are each independently selected from the group consisting of —H and —NH$_2$, with the proviso that at least 1 or 2 of X, Y, and Z are hydrogen, with an effective amount of 4-amino-1,2,4-triazole (ATA) to produce DATB or TATB or hydroxylamine or O-alkylhydroxylamine, where alkyl has 1 to 10 carbon atoms to primarily produce DATB;

in the presence of a strong base selected from sodium butoxide, potassium butoxide, potassium propoxide, sodium propoxide, sodium ethoxide, potassium ethoxide, sodium methoxide, potassium methoxide, and combinations thereof; in a solvent selected from the group consisting of methanol, ethanol, propanol, butanol, dimethylsulphoxide, N-methylpyrrolidone, hexamethylphosphoramide, dimethylformamaide, dimethylacetamide and mixtures thereof, provided that when alcohols are present or hydroxylamine or its O-alkyl derivatives replace ATA primarily DATB is formed; and (b) isolating the DATB or TATB produced.

In another aspect, the present invention concerns a process to produce 1,3-diamino-2,4,6-trinitrobenzene (DATB) or 1,3,5-triamino-2,4,6,-trinitrobenzene (TATB):

(a) by obtaining an aromatic compound of the structure:

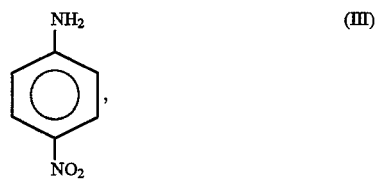

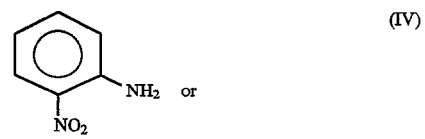

mixtures thereof from commercial sources or by:

(i) reacting

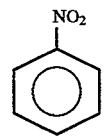

at a temperature of between about 0° and 50° C. for between about 0.1 and 24 hr with an effective amount of ATA, hydroxylamine or O-alkylhydroxylamine to produce mono or diamination, in the presence of a strong base selected from sodium butoxide, potassium butoxide, potassium propoxide, sodium propoxide, sodium ethoxide, potassium ethoxide, sodium methoxide, potassium methoxide, and combinations thereof;

in a solvent selected from the group consisting of dimethylsulphoxide, N-methylpyrrolidone, hexamethylphosphoramide, dimethylformamide, dimethylacetamide, or mixtures thereof, and isolating the product which is III;

(ii) or nitrating aniline using a mixture of nitric acid and sulfuric acid to produce structures III and IV; or (iii) nitrating acetanilide using a mixture of nitric acid and sulfuric acid to produce 4-nitroacetanilide and nitrating further using a mixture of nitric acid and sulfuric acid to produce VI;

(b) reacting 2-nitroaniline, 4-nitroaniline or combinations thereof with a nitric acid, and sulfuric acid mixture under conditions to produce 2,4,6-trinitroaniline (VI);

(A) reacting at ambient pressure and a temperature of between about 0° and 50° C. for between about 0.1 and 24 hr a trinitroaromatic compound of the structure:

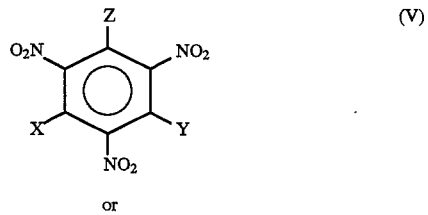

or

-continued

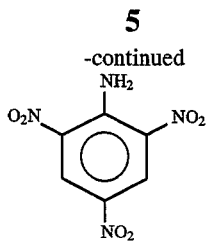

(VI)

wherein

X, Y, and Z are each independently selected from the group consisting of —H and —NH$_2$, with the proviso that at least 1 or 2 of X, Y, and Z is hydrogen;

with an effective amount of 4-amino-1,2,4-triazole, hydroxylamine or O-alkylhydroxylamine wherein alkyl contains 1 to 10 carbon atoms;

in the presence of a base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of methanol, ethanol, propanol, butanol, dimethylsulphoxide, N-methylpyrrolidone, hexamethylphosphoramide, dimethylformamide, dimethylacetamide, and mixtures thereof with the proviso that when alcohol is present or hydroxylamine and its O-alkyl derivatives replace ATA, primarily DATB is produced; and (B) isolating the DATB or TATB produced.

Preferably, DATB is produced when ATA, hydroxyl amine or O-alkylhydroxylamine is present in between about 1.9 and 2.3 molar equivalents per mole of structure V.

Preferably, structure V is selected from 1,3,5-trinitrobenzene, 2,4,6-trinitroaniline, or 1,3-diamino-2,4,6-trinitrobenzene.

Preferably, the strong base is selected from sodium methoxide or potassium tert-butoxide.

Preferably, the solvents are selected from methanol, ethanol, propanol, butanol, dimethylsulphoxide, N-methylpyrrolidone, hexamethylphosphoramide, dimethylformamide, dimethylacetamide and mixtures thereof, provided that when alcohols are present or hydroxylamine and its O-alkyl derivatives replace ATA, primarily DATB and picramide are formed.

Preferably, TATB is produced when ATA is present in between about 3.9 and 5.5 molar equivalents per mole of structure V.

DETAILED DESCRIPTION OF THE INVENTION AND PREFERRED EMBODIMENTS

Definitions

As used herein:

"Alkyl" refers to alkyl groups, having 1 to 10 carbon atoms and includes alkylaryl groups such as benzyl or ethylenephenyl (—CH$_2$CH$_2$-phenyl).

"ATA" refers to 4-amino-1,2,4-triazole.

"DATB" refers to 1,3-diamino-2,4,6-trinitrobenzene.

"DMSO" refers to dimethylsulphoxide.

"HMPA" refers to hexamethylphosphoramide.

"NB" refers to nitrobenzene.

"NMP" refers to N-methypyrrolidone.

"Picramide" or "TNA" refers to 1-amino-2,4,6-trinitrobenzene.

"TATB" refers to 1,3,5-triamino-2,4,6-trinitrobenzene.

"TNB" refers to 1,3,5-trinitrobenzene.

"TNT" refers to 2,4,6-trinitrotoluene.

In the present invention, the starting material, trinitrated benzene structure is contacted with strong base in the presence of one or more solvents at between about 0° and 50° C. and ambient pressure for between about 0.1 and 24 hr, preferably between about 1 and 12 hr, more preferably between about 1 and 5 hr. Preferably, the temperature is between about 10° and 30° C., and more preferably about ambient temperature (i.e. about 20° C.). The trinitrated aromatic compound is reacted with ATA.

A. Katritzky et al., *Journal of Organic Chemistry*, vol. 51, pp. 5039–5040 (1986) disclose the use of 4-amino-1,2,4-triazole (ATA) for direct mono-amination of a substituted mononitrobenzene. There is no teaching or suggestion to use ATA for the multiple amination of nitro benzenes having two or more nitro substituents.

The extent of the amination using 4-amino-1,2,4-triazole is normally controlled by judicious choice of temperature, time, solvents, strong base and amount of ATA. The amount of ATA reagent is also important to produce DATB, i.e. between about 1.9 and 2.3 molar equivalents per mole of compound V, preferably about 2.1 eq.

Hydroxylamine and its O-alkyl derivatives are also used to replace a stoichiometrically equivalent amount of ATA, and they produce primarily DATB.

Solvents—In the present invention, solvents which are preferred include dipolar aprotic solvents including, but not limited to, dimethylsulphoxide N-methylpyrrolidone, hexamethylphosphoramide, dimethylformamide, diethylforrhamide, dimethylacetamide and the like. The solvent may also include diluerits (benzene, chloroform) as needed to optimize conditions and product yields. Mixtures of solvents are also included.

Strong Bases—In the present invention, strong bases are usually the alkali metal salts of alcohols. Alcohols having 1–15 carbon atoms are preferred, more preferred are alcohols having 1–10 carbon atoms, and most preferably are alcohols having 1–6 carbon atoms. Especially preferred alcohols include methanol, ethanol, propanol, (n- or iso-) or butanol (n-, iso-, sec-, or tert-).

The following Examples are presented to be descriptive and illustrative only. They are not to be construed to be limiting in any way.

General

ATA or 4-amino-1,2,4-triazole is commercially available from Reilly Industries, Inc., 1500 South Tibbs Avenue, Indianapolis, Ind. 46242-0912.

Picramide is obtained from commercial sources or prepared according to E. Y. Spencer et al., *Canadian Journal Research*, vol. 24B, pp. 204–207 (1946).

1,3,5-Trinitrobenzene is obtained from commercial sources or prepared according to *Organic Synthesis*.

2,4,6-Trinitrotoluene is obtained from commercial sources or is prepared according to any literature source.

DMSO is dried and stored over 4A molecular sieves.

The reactions were performed in TEFLON® capped reaction vessels or reaction vessels equipped with drying tubes containing anhydrous calcium sulfate to protect VNS reactions from atmospheric moisture.

EXAMPLE 1

Preparation of DATB from Picramide Using Hydroxylamine (a) Hydroxylamine hydrochloride (0.709 g, 10.2 mmol) and picramide (0.477 g, 2.09 mmol) are dissolved in 17 ml DMSO. Sodium methoxide (1.28 g, 23.6 mmol) in methanol (5.40 ml) is added with stirring, and the resulting brown suspension is stirred at ambient temperature for 4 hr. The reaction mixture is poured into 200 ml of saturated aqueous ammonium chloride. The product is collected by filtration, washed with water and cold acetone to yield 0.139 g (27%) of a yellow solid. The IR spectra for this material and DATB are identical.

(b) Similarly, when Example 1(a) is repeated except that methanol is replaced by a volumetrically equivalent amount of ethanol, n-propanol, iso-propanol or tert-butanol, and sodium methoxide is replaced by a stoichiometrically equivalent amount of sodium ethoxide, sodium n-propoxide, sodium isopropoxide, or sodium tert-butoxide respectively, a similar amount of DATB is produced.

EXAMPLE 2

Preparation of PATB from Picramide Using O-methylhydroxylamine (a) DMSO (10 ml) is added with rapid stirring to a mixture of picramide (0.477 g, 2.09 mmol), O-methylhydroxylamine hydrochloride (0.709 g, 10.2 mmol) and sodium methoxide (1.27 g, 23.6 mmol). The dark brown suspension is stirred at ambient temperature for 2 hr. The reaction mixture is poured into cold 0.12N aqueous HCl (200 ml). The resulting precipitate is collected, washed with water and dried to yield 0.454 g (89%) of a yellow solid. The IR spectra for this material and DATB are identical.

(b) Similarly, when Example 2(a) is repeated except that sodium methoxide is replaced by a stoichiometrically equivalent amount of sodium ethoxide, sodium n-propoxide, sodium isopropoxide, or potassium tert-butoxide respectively, a similar amount of DATB is produced.

EXAMPLE 3

Preparation of DATB from Picramide Using O-Benzylhydroxylamine (a) DMSO (15 ml) is added with rapid stirring to a mixture of picramide (0.477 g, 2.09 mmol), O-benzylhydroxylamine (1.64 g, 10.3 mmol) and sodium methoxide (1.91 g, 35.4 mmol). The brown suspension is stirred at ambient temperature for 15 hr. The reaction mixture is poured into cold 0.12N aqueous HCl (200 ml). The resulting precipitate is collected, washed with water and dried to yield 0.444 g (87%) of DATB.

(b) Similarly, when Example 3(a) is repeated except sodium methoxide is replaced by a stoichiometrically equivalent amount of sodium ethoxide, sodium n-propoxide, sodium isopropoxide, or potassium tert-butoxide respectively, a similar amount of DATB is produced.

EXAMPLE 4

Preparation of TATB from TNB Using ATA (a) A suspension of sodium methoxide (1.19 g, 22.2 mmol) in DMSO (15 ml) is added to a solution of TNB (0.296 g, 1.39 mmol) and ATA (0.853 g, 10.2 mmol) in 4 ml DMSO with rapid stirring. The brown suspension is stirred for 2 hr at ambient temperature. The reaction mixture is poured into cold 0.12N aqueous HCl (200 ml). The resulting precipitate is collected, washed with water and dried to yield 0.353 g (98%) of a yellow solid. The IR spectra for this material and TATB are identical.

(b) Similarly, when Example 4(a) is repeated except sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 5

Preparation of TATB from DATB Using ATA (a) Sodium methoxide (0.600 g, 11.1 mmol) is added to a solution of DATB (0.25 g, 1.05 mmol) and ATA (0.429 g, 5.10 mmol) in 15 ml DMSO. The reddish brown suspension is stirred for 2.5 hr at ambient temperature. The reaction mixture is poured into cold 0.12N aqueous HCl (200 ml). The resulting precipitate is collected, washed with water and dried to yield 0.270 g (100%) of TATB.

(b) Similarly, when Example 5(a) is repeated except sodium methoxide is replaced by a stoichiometrically equivalent amount of sodium ethoxide, sodium n-propoxide, sodium isopropoxide, or pothssium tert-butoxide respectively, a similar amount of TATB is produced.

EXAMPLE 6

Preparation of TATB from Picramide Using ATA (a) Sodium methoxide (1.19 g, 22.0 mmol) is added to a solution of picramide (0.228 g, 1.00 mmol) and ATA (0.841 g, 10.0 mmol) in 15 ml DMSO. The reddish orange suspension is stirred for 3 hr at ambient temperature. The reaction mixture is poured into cold 0.12N aqueous HCL The resulting precipitate is collected, washed with water and dried to yield 0.236 g (91%) of TATB.

(b) Similarly, when Example 6(a) is repeated except sodium methoxide is replaced by a stoichiometrically equivalent amount of sodium ethoxide, sodium n-propoxide, sodium isopropoxide, or potassium tert-butoxide respectively, a similar amount of TATB is produced.

EXAMPLE 7

Preparation of Diamino-TNT (DATNT) from TNT (a) A suspension of sodium methoxide (1.19 g, 22.2 mmol) in 13 ml DMSO is added to a solution of TNT (0.476 g, 2.10 mmol) and ATA (0.853 g, 10.2 mmol) in 4 ml DMSO. The brown suspension is stirred for 3 hr at ambient temperature and then poured into a saturated aqueous solution of ammonium chloride (200 ml). A deep yellow solid is collected, washed with water and dried to give 0.337 g (62%) of DATNT: $^1$H-nmr (CDCl$_3$+DMSO–d$_6$) δ 8.44 (br, s, 4, NH$_2$) and 2.35 (s, 3, ARCH$_3$).

(b) Similarly, when Example 7(a) is repeated except sodium methoxide is replaced by a stoichiometrically equivalent amount of sodium ethoxide, sodium n-propoxide, sodium isopropoxide, or potassium tert-butoxide respectively, a similar amount of DATNT is produced.

While only a few embodiments of the present invention have been shown and described herein, it is apparent to those skilled in the art that various modifications and changes can be made in these novel processes using ATA or hydroxylamine or O-alkyl hydroxylamine derivatives to produce DATB or TATB without departing from the spirit and scope of the present invention. All such modifications and changes coming within the scope of the appended claims are intended to be covered thereby. In this application, primarily means that DATB or TATB is produced in about 70% yield, perferably more than about 80% yield, and more preferably 90% or greater.

We claim:
1. A process to produce 1,3,5-triamino-2,4,6,-trinitrobenzene (TATB), which process comprises:
(a) reacting at ambient pressure and a temperature of between about 0° and 30° C. for between about 0.1 and 24 hr, a trinitroaromatic starting material compound of the structure:

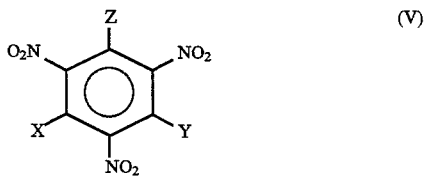

wherein
X, Y, and Z are each independently selected from the group consisting of —H and —NH$_2$, with the proviso that at least 1 of X, Y, and Z is hydrogen;
with an effective amount of 4-amino-1,2,4-triazole;
in the presence of a strong base selected from sodium butoxide, potassium butoxide, potassium propoxide, sodium propoxide, sodium ethoxide, potassium ethoxide, sodium methoxide, potassium methoxide, or combinations thereof;
in a solvent selected from the group consisting of dimethylsulphoxide, N-methylpyrrolidone, hexamethylphosphoramide, dimethylformamide, dimethylacetamide and mixtures thereof; and
(b) isolating the TATB produced.
2. The process of claim 1 wherein the reaction temperature is between about 10° and 30° C.; and 4-amino-1,2,4-triazole is used.
3. The process of claim 2 wherein DATB is produced and the 4-amino-1,2,4-triazole is present in step (a) in between about 1.9 and 2.3 molar equivalents per mole of the trinitroaromatic starting material compound.
4. The process of claim 1 wherein the trinitroaromatic starting material compound is selected from 1,3,5-trinitrobenzene, 2,4,6-trinitroaniline, or 1,3-diamino-2,4,6-trinitrobenzene.
5. The process of claim 1 wherein the 4-amino-1,2,4-triazole is present in about 2.1 mole eq.
6. The process of claim 1 wherein the strong base is sodium methoxide or potassium tert-butoxide.
7. The process of claim 1 wherein:
the starting material compound is selected from 1,3,5-trinitrobenzene or 2,4,6-trinitroaniline;
the strong base is selected from sodium methoxide or potassium tert-butoxide; and
the solvent is DMSO.
8. The process of claim 2 wherein TATB is produced and the 4-amino-1,2,4-triazole is present in between about 3.9 and 5.5 molar equivalents per mole of the trinitroaromatic starting material compound.
9. The process of claim 8, wherein the trinitroaromatic starting material compound is selected from 1,3,5-trinitrobenzene, 2,4,6-trinitroaniline, or 1,3-diamino-2,4,6-trinitrobenzene.
10. The process of claim 8 wherein the 4-amino-1,2,4-triazole is present in about 4.5 mole eq.
11. The process of claim 8 wherein the strong base is sodium methoxide.
12. The process of claim 8 wherein the solvent is a dipolar aprotic solvent selected from dimethylsulphoxide, N-methylpyrrolidone, hexamethylphosphoramide, dimethylformamide, dimethylacetamide, or mixtures thereof.

13. The process of claim 8 wherein the trinitroaromatic starting material compound is selected from 1,3,5-trinitrobenzene, 2,4,6-trinitroaniline, or 1,3-diamino-2,4,6-trinitrobenzene;
the strong base is selected from sodium methoxide and the solvent is selected from dimethylsulphoxide, N-methylpyrrolidone, hexamethylphosphoramide, dimethylformamide, dimethylacetamide or mixtures thereof.
14. The process of claim 1 wherein 4-amino-1,2,4-triazole is used in between about 1.9 and 2.3 molar equivalents or between about 3.9 and 5.5 equivalents per mole of compound V;
the temperature is between about 10° and 30° C.;
the strong base is sodium methoxide or potassium tert-butoxide; and
the solvent is dimethylsulphoxide.
15. The process of claim 1 wherein 4-amino-1,2,4-triazole is used in between about 1.9 and 2.3 molar equivalents or between about 3.9 and 5.5 equivalents per mole of said trinitroaromatic starting material compound;
the strong base is selected from sodium methoxide or potassium tert-butoxide; and
the solvent is dimethylacetamide.
16. The process of claim 1 wherein the solvent is hexamethylphosphoramide.
17. The process of claim 1 wherein:
the starting material is selected from 2,4,6-trinitroaniline or 1,3-diamino-2,4,6-trinitrobenzene;
the strong base is sodium methoxide or potassium tert-butoxide, and
the temperature of the reaction is between about 10° and 30° C.
18. A process to produce 1,3,5-triamino-2,4,6,-trinitrobenzene (TATB), which process comprises:
(a) obtaining an aromatic starting material compound of the structure:

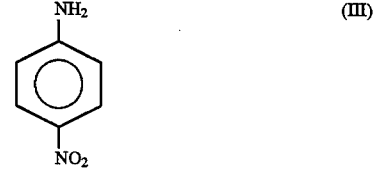

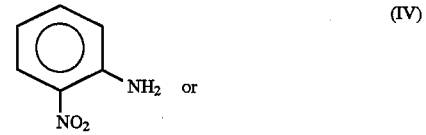

mixtures thereof from commercial sources or by:
(i) reacting ph—NO$_2$ with an amount of 4-amino-1,2,4-triazole effective to produce 4-nitroaniline;
in the presence of a strong base selected from sodium butoxide, potassium butoxide, potassium propoxide, sodium propoxide, sodium ethoxide, potassium ethoxide, sodium methoxide, potassium methoxide, and combinations thereof;
in a solvent selected from the group consisting of dimethylsulphoxide, N-methylpyrrolidone, hexamethylphosphoramide, dimethylformamide, dimethylacetamide, or mixtures thereof, or isolating the product which is III;

(ii) or nitrating aniline using a mixture of nitric acid and sulfuric acid to produce compounds III and IV; or (iii) nitrating acetanilide using a mixture of nitric acid and sulfuric acid to produce 4-nitroacetanilide and nitrating further using a mixture of nitric acid and sulfuric acid to produce compound VI;

(b) reacting 2-nitroaniline, 4-nitroaniline or combinations thereof with a nitric acid and sulfuric acid mixture under conditions to produce 2,4,6-trinitroaniline;

(A) reacting at temperature of between about 0° and 30° C. for between about 0.1 and 24 hr a trinitroaromatic starting material compound:

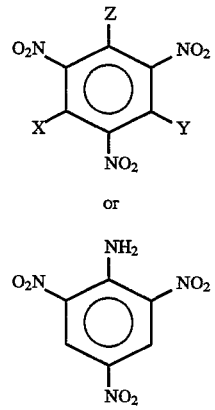

(V)

or (VI)

wherein

X, Y, and Z are each independently selected from the group consisting of —H and —NH$_2$, with the proviso that at least 1 of X, Y, and Z is hydrogen;

with an effective amount of 4-amino-1,2,4-triazole;

in the presence of a strong base selected from the group consisting of sodium butoxide, potassium butoxide, potassium propoxide, sodium propoxide, sodium ethoxide, potassium ethoxide, sodium methoxide, potassium methoxide, and mixtures thereof;

in a solvent selected from the group consisting of dimethylsulphoxide, N-methylpyrrolidone, hexamethylphosphoramide, dimethylformamide, dimethylacetamide, and mixtures thereof; and (B) isolating the 1,3,5-triamino-2,4,6-trinitrobenzene produced.

19. The process of claim 18 wherein 4-amino-1,2,4 triazole is used in between about 1.9 and 2.3 molar equivalents or between about 3.9 and 5.5 equivalents per mole of compound V;

the temperature is between 10° and 30° C.;

the time is between about 0.1 and 24 hr;

the strong base is sodium methoxide or potassium tert-butoxide; and the solvent is dimethylsulphoxide.

20. The process of claim 18 wherein the reaction temperature is between about 10° and 30° C.

* * * * *